United States Patent [19]

McConnell

[11] 4,029,103
[45] June 14, 1977

[54] ANCHORING PLATE FOR MEDICAL TUBES

[76] Inventor: Francis P. McConnell, 515 Brook St., Mamaroneck, N.Y. 10543

[22] Filed: Aug. 11, 1975

[21] Appl. No.: 603,301

[52] U.S. Cl. .................... 128/348; 128/DIG. 26
[51] Int. Cl.² ................................... A61M 25/00
[58] Field of Search ............. 128/214 R, 133, 348, 128/349, 350, DIG. 26; 24/115 H, 81 CC; 206/68

[56] References Cited

UNITED STATES PATENTS

| 268,407 | 12/1882 | Hughes | 24/115 H |
|---|---|---|---|
| 2,727,513 | 12/1955 | Muller | 128/133 |
| 3,046,988 | 7/1962 | Moreau et al. | 128/349 B X |
| 3,368,564 | 2/1968 | Selix | 128/348 |
| 3,568,679 | 3/1971 | Reif | 128/349 |
| 3,630,195 | 12/1971 | Santomieri | 128/DIG. 26 X |
| 3,696,920 | 10/1972 | Lahay | 128/DIG. 26 X |
| 3,702,612 | 11/1972 | Schlesinger | 128/350 R |
| 3,834,380 | 9/1974 | Boyd | 128/DIG. 26 X |
| 3,942,528 | 3/1976 | Loeser | 128/133 X |

Primary Examiner—Stephen C. Pellegrino
Attorney, Agent, or Firm—Edward J. Handler, III; Jamie S. Smith

[57] ABSTRACT

A device for anchoring and directing medical tubing comprising a plate of flexible resilient material having an internal curved passageway(s), open at both ends, with a cross sectional area at least in segments thereof no greater than the cross sectional area of the tubes to be anchored. Each passageway communicates with a face of the plate by means of a slit or cut extending from the passageway wall to the surface of the plate along the entire length of the passageway. The plate may also be provided with slots remote from each other and from the passageway and extending completely through the plate, and with an elastic belt adapted to affix the plate to a patient by passing through one such slot, over the slit surface of the plate, through the other slot and around a member of the patient's body.

14 Claims, 7 Drawing Figures

ANCHORING PLATE FOR MEDICAL TUBES

BACKGROUND OF THE INVENTION

1. Field of the Invention

This invention relates generally to anchoring plates for medical tubes, and more particularly relates to a device which protects and directs the external portion of medical tubes that are partially interior to and partially exterior to a patient's body.

2. DESCRIPTION OF THE PRIOR ART

Many medical procedures involve attachment over a period of time of medical infusion or drainage tubes to the body of a patient such that one portion of the tube contacts an internal organ of the patient, while another portion of the tube is external to the patient's body. For example, certain medical procedures involve the use of intravenous infusion tubing, catheters, including nephrostomy tubing, tubing for drainage of surgical wounds, and the like.

It is often desirable to change the direction of the tubing as it exits from the patent's body in order, for example, to avoid the area of an incision or to lead into a receptacle for fluids.

Hospital technique for attaching such tubing to the patient has in the past generally involved using layers of adhesive tape. Typically, the patient's skin is prepared by treatment with benzoin, which improves adhesion of the adhesive, but causes considerable discomfort to the patient. A base layer of tape is then placed on the prepared skin near the point of exit of the tube from the body, the tube is laid over this tape and redirected if necessary, and a second layer of tape is placed over the tube to hold it in position. If more than one tube is employed, each additional tube is placed individually on the tape covering the previous tube and is itself then secured with another layer of adhesive tape.

The above procedure is characterized by a number of significant disadvantages. The adhesive tape is irritating to the patient's skin and is rejected by it after several days. At this time, the rejected tape must be removed from the patient and tubes, and new tape applied. This procedure is difficult and time consuming, in particular because the adhesive tape is very difficult to remove from the latex rubber medical tubes which are commonly employed, and puncturing or tearing of the tubes may even occur during the removal procedure. The use of quantities of adhesive also can complicate cleaning of the incision, restrict air circulation near the incision, and make the ends of the medical tubing relatively inaccessible.

While various guides, holders and supports have been proposed for medical tubing, many prior art devices have been characterized by problems and disadvantages. For example, often these devices fail to provide for redirection of the tubing while adequately protecting it. Many such devices continue to rely solely on adhesive, with all its disadvantages, for attachment of the holder to the patient. Others are unduly bulky. Certain of the proposed devices would not protect the medical tubing from snagging on clothing, or would not allow freedom of movement for the patient while preventing the tubes from dislodging. A number of the devices that have been proposed lack multi-tube capacity, and some may not adequately prevent creep of the tubing into or out of the body. Examples of prior art devices which exhibit some or all of these disadvantages may be found in U.S. Pat. Nos. 3,834,380; 3,368,564; 3,568,679; 3,630,195; 3,696,920; and 3,702,612.

SUMMARY OF THE INVENTION

It is a major object of the present invention to provide an anchoring plate for medical tubes which avoids the disadvantages of the prior art proposals by directing the tubes near the incision and at the same time immobilizing and protecting the tubes near the incision so that they can neither be torn out of the incision nor creep into it. The tube anchoring plate is lightweight, comfortable, impervious to alcohol and other common hospital solutions and potentially washable, capable of sterilization by autoclaving or the like and reusable. It significantly reduces or eliminates the amount of adhesive tape in contact with skin or tubing, so that the problem which arise from contact of adhesive with the patient's skin or with the tubes themselves may be avoided. In addition, the use of the instant invention for anchoring medical tubes facilitates cleaning of the incision, including behind the plate, allows for visual observation of the whole tube, keeps the ends of the tubes accessible, allows air to circulate around the incision, reduces the bulk of the dressing, and allows the patient to bathe, shower, swim and generally engage in a full range of normal physical activities. The tube anchoring plate may be placed in position or replaced quickly and easily, even by non-professionals as in home care.

Additional objects and advantages of the present invention will be more fully understood from the following description and drawings.

In general, the device comprises a multi-faced plate, meaning as used herein a body substantially thinner in one dimension than in another, having an internal curved passageway or passageways which are positioned substantially in a plane containing the long dimension of the plate and which have a cross sectional area at least in segments thereof no greater than the cross sectional area of the tubes to be anchored resulting in an interference fit. Each passageway communicates longitudinally with a surface of the plate by means of a slit, cut or combination thereof extending from the passageway wall to the surface of the plate along the passageway's entire length. Each passageway is open at each end thereof. The plate is formed of flexible resilient material so that the surface of the plate may be separated at the slit and the tubing inserted into the conduit through this opening, and so that the plate will return to its original conformation after this insertion of the tubing.

The plate is affixed to the patient's body preferably after it is positioned slit-side up on the desired body area, usually near the incision, and after the tubes are inserted into the passageways through the slits as described above. While the plate may be affixed to the patient using a small amount of adhesive or other attaching means, it is preferred that the plate have two slots through it, remote from each other and from the conduits, so that an elastic belt may be passed through one slot, over the slit surface of the plate, through the other slot and around a member of the patient's body in order to secure the plate to the patient.

DESCRIPTION OF THE PREFERRED EMBODIMENTS

Figure 1:
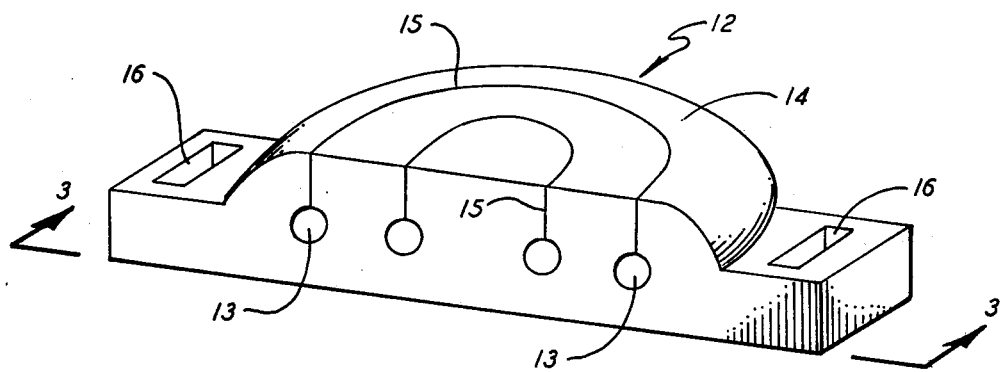
FIG. 1 is a perspective view of a preferred embodiment of the medical tube anchoring plate of this invention illustrating two curved passageways which make a 180° turn, and slots for passage of an elastic belt.
Figure 2:
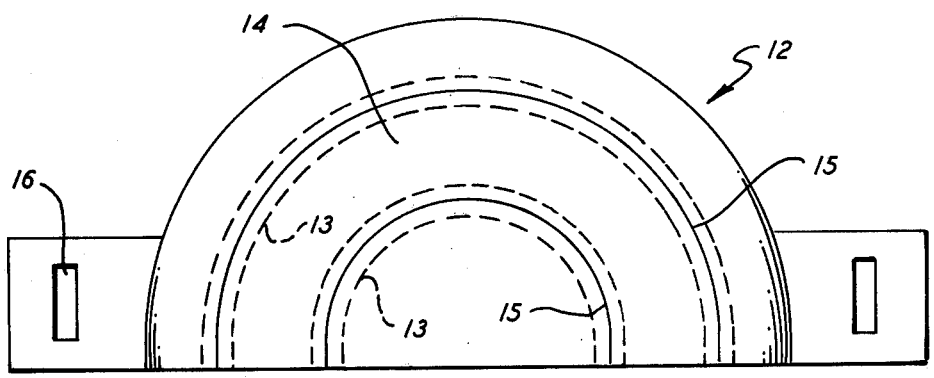
FIG. 2 is a top view of the device of FIG. 1.
Figure 3:
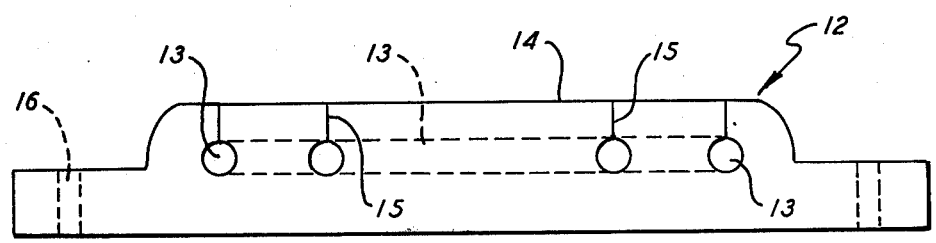
FIG. 3 is a plan view of the tube anchoring plate looking in the direction of arrows 3—3 in FIG. 1.
Figure 4:
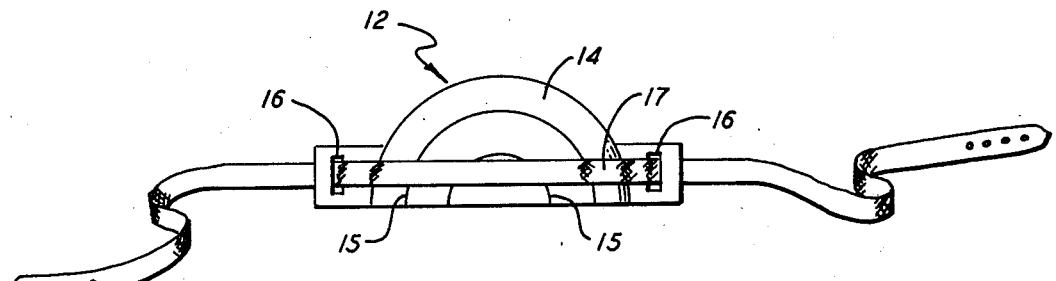
FIG. 4 is a top view of the tube anchoring plate with the elastic belt inserted through the slots in the plate.

Referring to FIGS. 1, 2 and 3 it can be seen that the device of this invention comprises a multi-faced plate, or body substantially thinner in one dimension than in another, 12 formed of flexible, resilient material. The plate contains internal curved passageways 13 open at each end thereof and of a cross sectional area no greater than the cross sectional area of the tubing to be anchored. The passageways are thus adapted to immobilize through an interference fit the portion of the medical tubing contained therein. Each passageway 13 communicates longitudinally with a surface of the plate 14 by means of a slit or cut 15 extending from the passageway wall to the surface of the plate along the entire length of the passageway. Each passageway 13 of FIGS. 1-3 defines a 180° curve for directing the tubing.

Preferably, the plate of this invention has more than one internal curved passageway 13 in order to accommodate two or more separate medical tubes at one time. It is also preferred that the passageways within the plate be completely covered by the surface of the plate 14, and in particular that the slits 15 in the surface of the plate constitute cuts of minimal width so that the plate surface 14 completely covers over the tubing once it is inserted in the passageway. This serves to protect the tubes and secure them in position.

Since it may be desirable to lap adhesive tape over the slit surface of the plate once the tubes are inserted in order to provide additional protection against dislodging of the tubes, as one embodiment the slit surface 14 of the plate is substantially flat so as to offer ample contact area for the adhesion of the tape.

Referring to FIGS. 1, 2, 3, and 4, the plate 12 is preferably also provided with slots 16, generally two, remote from each other and from the passageways and extending completely through the plate such that an elastic belt 17 may be passed through one slot 16, over the slit surface of the plate 14, through the other slot 16 and around a member of the patient's body. The belt then serves to secure the plate to the patient and also to provide an additional safeguard against accidental freeing of the tubes from the passageways.

Figure 5:
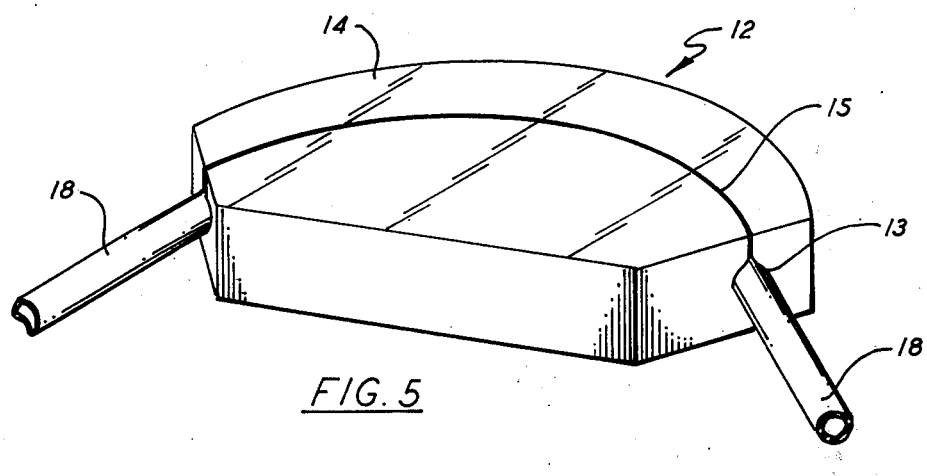
FIG. 5 is a perspective view of an alternative embodiment of this invention showing a single curved passageway which makes a 90° turn and a tube contained therein.

Plate 12 may alternatively contain only a single passageway and slit as shown in FIG. 5. FIG. 5 also illustrates other alternatives in the embodiment of the present invention. The curved passageway 13 may curve in varying extents and thus cause the portions of the tube 18 exiting its ends to form various angles with each other. It is contemplated by the present invention that the passageway may direct the tubing so as to deviate from its entry direction by an angle ranging from 45° up to 180°. In FIG. 5 a turn of 90° is illustrated. Also, the slit 15 may have appreciable width so that the slit surface 14 of the plate exhibits a crack running along the course of the slit or so that the combination of slot and slit or zipper effect is accomplished.

A tube 18 is shown inserted in the passageway 13 of the plate in FIG. 5. The tube 18 may be inserted in the plate by separating the slit surface of the plate 14 at the slit 15 and placing the tube in position in the passageway 13 or by pressing the tube down into the slit, thus causing the slit surface to separate at the slit, and further pressing the tube into the passageway. The tube may be removed from the plate by reversing this procedure. After the tube is placed into or removed from the passageway of the plate, the natural resiliency of the plate material causes it to return to essentially its original configuration.

The plate 12 is formulated of a material providing flexibility and resilience so that insertion and removal of the medical tubing is simplified, and so that the plate will conform to some extent to the member of the patient's body to which it is attached. The material must provide sufficient strength to the plate so that it is resistant to tearing and separation in use. In general, many materials such as nylon, polyethylene, polypropylene, polyurethane, neoprene, styrene, and other semi-rigid foams and synthetic rubbers, cast or pressed into the desired shape, would provide the necessary properties for the medical tube anchoring plate of the present invention. Silicone rubber, especially RTV (trade name for silicon rubber) is the preferred material. The plate may be integrally formed of the chosen material or may be formed in several parts of one or more materials.

Figure 6:
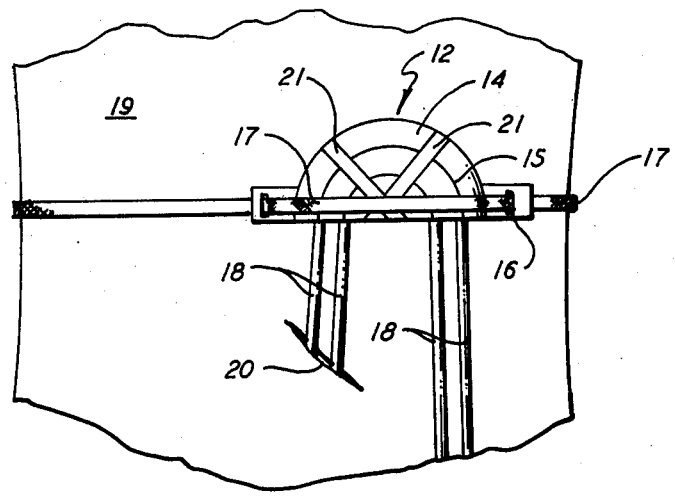
FIG. 6 shows the tube anchoring plate in position on a patient with adhesive tape lapped over the slit surface of the plate, and the elastic belt holding the plate in place.

FIG. 6 depicts a preferred embodiment of the present invention with the medical tubing plate 12 attached to a member of the patient's body 19. The plate is of a size adapted to the size of the member to which it is to be attached.

For purposes of illustration, the plate is shown in FIG. 6 employed as a nephrostomy plate on the back of a patient who has undergone a nephrostomy operation. Tubing 18 exits the surgical wound 20 and is secured in the curved passageways of the plate. The tubes are directed 180° by the curvature of the passageways. Two strips of adhesive tape 21 are placed over the slits 15 of the plate, and the ends of the strips are lapped over onto the back of the plate so that the adhesive does not touch the patient's body. An elastic belt 17 passes through the slots 16 over the slit surface of the plate 14 and around the patient's torso 19. The plate of the present invention is particularly useful as a nephrostomy plate because it provides for redirection of the tubes while immobilizing them above the incision so that the immobilization means (the plate and belt) does not irritate the incision.

Figure 7:
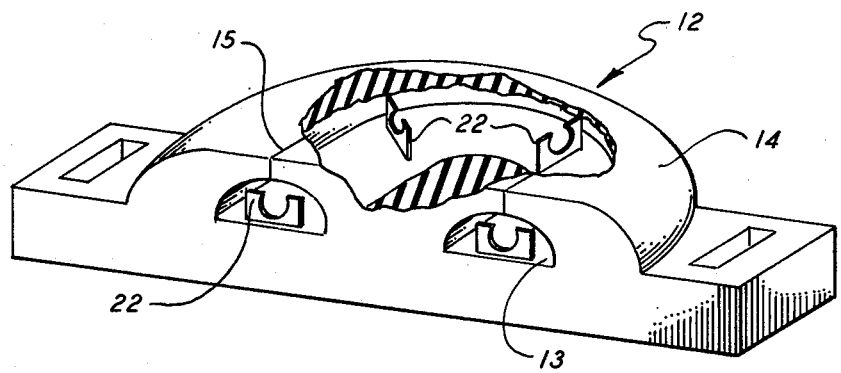
FIG. 7 is a perspective view with the surface partially cut away showing an alternative embodiment of this invention with clips within the passageways comprising the segments of the passageways having a cross sectional area no greater than the cross sectional area of the tubes.

FIG. 7 illustrates a further alternative embodiment of the present invention in which the passageway 13 immobilizes the tubing by an interference fit only along segments of the passageway by means of clips 22 or other local constrictions. The tubing is protected along its entire length by the walls of the passageway.

Although this invention is illustrated and described with emphasis on certain embodiments it should be understood that the scope of the invention is indicated by the appended claims and that all changes that come within the meaning and range of equivalency of the claims are to be embraced therein.

I claim:

1. A device for anchoring through an interference fit and directing medical tubing comprising a multi-faced plate of flexible, resilient material having
   a. at least one internal curved passageway with a cross sectional area at least in segments thereof no longer than the cross sectional area of the tubing to be anchored, open at its ends to at least one face of said plate, and
   b. a slit communicating a face of said plate with said passageway along its entire length, wherein the plate is provided with two slots remote from each other and from the passageway and extending completely through the plate, and wherein the device further comprises a belt adapted to pass through one slot, over the slit face of the plate which is in communication with the passageway, through the other slot, and around a convenient member of a patient, so as to provide an additional safeguard against accidental freeing of the tubing from the passageway.

2. A device for anchoring and directing medical tubing as in claim 1 wherein the plate has more than one internal curved passageway.

3. A device for anchoring and directing medical tubing as in claim 1 wherein the curved passageway defines a turn of about 180°.

4. A device for anchoring and directing medical tubing as in claim 1 wherein the flexible, resilient material is silicone rubber.

5. A device for anchoring and directing medical tubing as in claim 1 wherein only some segments of the passageway have a cross sectional area no greater than the cross sectional area of the tubing to be anchored.

6. A device for anchoring and directing medical tubing as in claim 5 wherein the segments of the passageway having a cross sectional area no greater than the cross sectional area of the tubing to be anchored comprise clips.

7. A device for anchoring through an interference fit and directing medical tubing, suitable for use on a physically active patient, comprising:
   a. a multi-faced plate formed of flexible, resilient material which tends to return to its original conformation after displacement, having:
      i. at least one internal curved passageway with a cross sectional area at least in segments thereof no larger than the cross sectional area of the tubing to be anchored, open at its ends to at least one face of said plate, and
      ii. a slit communicating a face of said plate with said passageway along its entire length;
   b. a non-adhesive belt means attached to said plate and adapted to pass around a convenient member of a patient to secure the device to the patient; and
   c. a means affixed to said plate, selected from the group consisting of adhesive tape and a portion of said belt, which is placed over the slit surface of the plate so as to provide an additional safeguard against accidental freeing of the tubing from the passageway.

8. A device for anchoring and directing medical tubing as in claim 7 wherein the plate has more than one internal curved passageway.

9. A device for anchoring through an interference fit and directing medical tubing comprising a multi-faced plate of flexible, resilient material having
   a. at least one internal curved passageway with a cross sectional area at least in segments thereof no larger than the cross sectional area of the tubing to be anchored, open at its ends to at least one face of said plate, and
   b. a cut communicating a face of said plate with said passageway along its entire length, wherein only some segments of said passageway, comprising clips, have a cross sectional area no greater than the cross sectional area of the tubing to be anchored.

10. A device for anchoring and directing medical tubing as in claim 7 wherein the curved passageway defines a turn of about 180°.

11. A device for anchoring and directing medical tubing as in claim 7 wherein the flexible, resilient material is silicone rubber.

12. A device for anchoring and directing medical tubing as in claim 7 wherein only some segments of the passageway have a cross sectional area no greater than the cross sectional area of the tubing to be anchored.

13. A device for anchoring and directing medical tubing as in claim 12 wherein the segments of the passageway having a cross sectional area no greater than the cross sectional area of the tubing to be anchored comprise clips.

14. A device for anchoring and directing medical tubing comprising:
   a. a multi-faced plate of silicon rubber having:
      i. two internal curved passageways both open at both ends thereof, defining turns of 180°, and both having cross sectional areas no greater than the cross sectional area of the tubes to be anchored;
      ii. slits of minimal width communicating a face of the plate with each passageway along the entire length of each passageway;
      iii. two slots remote from each other and from the passageways and extending completely through the plate; and
   b. an elastic belt adapted to pass through one slot, over the slit face of the plate, through the other slot, and around a convenient member of the patient, so as to provide an additional safeguard against accidental freeing of the tubing from the passageway.

* * * * *